(12) United States Patent
Burton et al.

(10) Patent No.: US 7,745,509 B2
(45) Date of Patent: Jun. 29, 2010

(54) POLYMER COMPOSITIONS WITH BIOACTIVE AGENT, MEDICAL ARTICLES, AND METHODS

(75) Inventors: Scott A. Burton, Woodbury, MN (US); Patrick D. Hyde, Burnsville, MN (US); Prabhakara S. Rao, Maplewood, MN (US); Caroline M. Ylitalo, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/728,439

(22) Filed: Dec. 5, 2003

(65) Prior Publication Data

US 2005/0124724 A1 Jun. 9, 2005

(51) Int. Cl.
C08K 9/10 (2006.01)
C08K 3/22 (2006.01)
A61L 15/00 (2006.01)

(52) U.S. Cl. ............... 523/122; 523/205; 524/430; 524/431; 524/432; 524/571; 524/575; 424/617

(58) Field of Classification Search ............... 523/122, 523/205; 524/430, 431, 916, 432; 424/617
See application file for complete search history.

(56) References Cited

U.S. PATENT DOCUMENTS

| | | | |
|---|---|---|---|
| 2,396,514 A | 3/1946 | Kreidl et al. | |
| 2,521,713 A | 9/1950 | Goetz | 167/14 |
| 2,689,809 A | 9/1954 | Fessler | |
| 2,736,721 A | 2/1956 | Dexter | 260/42 |
| 2,791,518 A | 5/1957 | Stokes et al. | |
| 2,934,066 A | 4/1960 | Stowasser | |
| 3,092,552 A | 6/1963 | Romans | |
| 3,380,848 A | 4/1968 | Horowitz | |
| 3,685,993 A | 8/1972 | Mukherjee | 96/33 |
| 3,761,590 A | 9/1973 | Fox, Jr. | |
| 3,800,792 A | 4/1974 | McKnight et al. | 128/156 |
| 3,841,953 A | 10/1974 | Lohkamp et al. | 161/150 |
| 3,911,115 A | 10/1975 | Hadhanyi | 424/180 |
| 4,024,312 A | 5/1977 | Korpman | 428/343 |
| 4,340,043 A | 7/1982 | Seymour | 128/132 |
| 4,528,321 A | 7/1985 | Allen et al. | 524/761 |
| 4,590,227 A | 5/1986 | Nakamura et al. | 523/130 |
| 4,592,920 A | 6/1986 | Murtfeldt | |
| 4,603,152 A | 7/1986 | Laurin et al. | 604/265 |
| 4,646,730 A | 3/1987 | Schonfeld et al. | 728/156 |
| 4,652,465 A | 3/1987 | Koto et al. | 427/216 |
| 4,728,323 A | 3/1988 | Matson | |
| 4,768,503 A | 9/1988 | Highgate et al. | |
| 4,892,528 A | 1/1990 | Suzuki et al. | 604/385 |
| 4,902,503 A | 2/1990 | Umemura et al. | |
| 4,902,565 A | 2/1990 | Brook | |
| 4,906,466 A | 3/1990 | Edwards et al. | |
| 4,921,704 A | 5/1990 | Fabo | 424/446 |
| 5,075,373 A | 12/1991 | Takemori et al. | 525/57 |
| 5,176,952 A | 1/1993 | Joseph et al. | 428/284 |
| 5,209,971 A | 5/1993 | Babu et al. | 428/343 |
| 5,214,119 A | 5/1993 | Leir et al. | 528/28 |
| 5,232,748 A | 8/1993 | Horowitz et al. | |
| 5,270,358 A | 12/1993 | Asmus | 524/55 |
| 5,326,567 A | 7/1994 | Capelli | 424/405 |
| 5,340,363 A | 8/1994 | Fabo | 604/304 |
| 5,369,155 A | 11/1994 | Asmus | 524/55 |
| 5,389,092 A | 2/1995 | Guillemet et al. | 604/304 |
| 5,393,831 A | 2/1995 | Hudson | |
| 5,409,472 A | 4/1995 | Rawlings et al. | 604/307 |
| 5,413,788 A | 5/1995 | Edwards et al. | |
| 5,418,257 A | 5/1995 | Weisman | 521/54 |
| 5,429,819 A | 7/1995 | Oka et al. | 424/400 |
| 5,432,000 A | 7/1995 | Young, Sr. et al. | |
| 5,437,932 A | 8/1995 | Ali et al. | 428/461 |
| 5,454,886 A | 10/1995 | Burrell et al. | |
| 5,458,877 A | 10/1995 | Obayashi et al. | |
| 5,470,585 A | 11/1995 | Gilchrist | |
| 5,476,712 A | 12/1995 | Hartman et al. | 428/317 |
| 5,512,041 A | 4/1996 | Bogart | 602/58 |
| 5,516,581 A | 5/1996 | Kreckel et al. | 428/317 |
| 5,567,779 A | 10/1996 | Sackmann et al. | 525/329 |
| 5,681,575 A | 10/1997 | Burrell et al. | |
| 5,681,579 A | 10/1997 | Freeman | 424/448 |
| 5,693,624 A | 12/1997 | Hardy et al. | |
| 5,695,857 A | 12/1997 | Burrell et al. | |
| 5,709,870 A | 1/1998 | Yoshimura et al. | |

(Continued)

FOREIGN PATENT DOCUMENTS

CN 1241662 A 1/2000

(Continued)

OTHER PUBLICATIONS

Full English-language translation of CN 138102A, Aug. 15, 2001.*

(Continued)

Primary Examiner—Vickey Nerangis
(74) Attorney, Agent, or Firm—Trisha D. Adamson

(57) ABSTRACT

A polymer composition that includes a hydrophilic polymer, an optional secondary organic polymer, and a bioactive agent distributed therein, wherein the bioactive agent is selected from the group consisting of a silver compound, a copper compound, a zinc compound, and combinations thereof.

23 Claims, No Drawings

U.S. PATENT DOCUMENTS

| | | | | |
|---|---|---|---|---|
| 5,744,151 | A | 4/1998 | Capelli | 424/405 |
| 5,750,134 | A | 5/1998 | Scholz et al. | 424/434 |
| 5,770,255 | A | 6/1998 | Burrell et al. | |
| 5,803,086 | A | 9/1998 | Scholz et al. | 128/849 |
| 5,830,496 | A | 11/1998 | Freeman | |
| 5,844,013 | A | 12/1998 | Kenndoff et al. | 521/137 |
| 5,848,995 | A | 12/1998 | Walder | 604/265 |
| 5,897,694 | A | 4/1999 | Woolf | 106/31 |
| 5,958,440 | A | 9/1999 | Burrell et al. | |
| 5,985,308 | A | 11/1999 | Burrell et al. | |
| 6,017,553 | A | 1/2000 | Burrell et al. | |
| 6,039,940 | A | 3/2000 | Perrault et al. | 424/78 |
| 6,087,549 | A | 7/2000 | Flick | |
| 6,103,152 | A | 8/2000 | Gehlsen et al. | 264/45 |
| 6,126,931 | A | 10/2000 | Sawan et al. | 424/78 |
| 6,130,303 | A | 10/2000 | Neff et al. | 526/306 |
| 6,156,678 | A | 12/2000 | Mukaida et al. | 442/118 |
| 6,194,332 | B1 | 2/2001 | Rock et al. | |
| 6,201,164 | B1 | 3/2001 | Wulff et al. | 602/48 |
| 6,217,889 | B1 | 4/2001 | Lorenzi et al. | |
| 6,267,590 | B1 | 7/2001 | Barry et al. | |
| 6,270,792 | B1 | 8/2001 | Guillemet et al. | 424/443 |
| 6,277,892 | B1 | 8/2001 | Deckner et al. | 514/772 |
| 6,284,362 | B1 | 9/2001 | Takai et al. | 428/326 |
| 6,288,076 | B1 | 9/2001 | Kostyniak et al. | 514/299 |
| 6,297,335 | B1 | 10/2001 | Funk et al. | 526/317 |
| 6,333,093 | B1 | 12/2001 | Burrell et al. | |
| 6,355,858 | B1 | 3/2002 | Gibbins | 602/41 |
| 6,379,791 | B1 | 4/2002 | Cernohous et al. | 428/355 |
| 6,436,420 | B1 * | 8/2002 | Antelman | 424/404 |
| 6,458,877 | B1 * | 10/2002 | Ahmed et al. | 524/275 |
| 6,468,521 | B1 | 10/2002 | Pedersen et al. | 424/78 |
| 6,548,727 | B1 | 4/2003 | Swenson | 602/41 |
| 6,582,711 | B1 | 6/2003 | Asmus et al. | 424/405 |
| 6,592,888 | B1 | 7/2003 | Jensen et al. | |
| 6,605,751 | B1 | 8/2003 | Gibbins et al. | 602/41 |
| 6,669,981 | B2 | 12/2003 | Parsons et al. | |
| 6,716,895 | B1 | 4/2004 | Terry | |
| 6,797,743 | B2 | 9/2004 | McDonald et al. | |
| 6,838,078 | B2 | 1/2005 | Wang et al. | 424/78 |
| 6,843,784 | B2 | 1/2005 | Modak et al. | |
| 7,285,576 | B2 | 10/2007 | Hyde et al. | |
| 2001/0010016 | A1 | 7/2001 | Modak et al. | 623/42 |
| 2002/0051823 | A1 | 5/2002 | Yan et al. | |
| 2002/0073891 | A1 | 6/2002 | Parsons et al. | |
| 2002/0156150 | A1 | 10/2002 | Williams et al. | |
| 2003/0021832 | A1 | 1/2003 | Scherr | 424/445 |
| 2003/0032765 | A1 | 2/2003 | McDonald et al. | |
| 2003/0049300 | A1 | 3/2003 | Terry | 424/423 |
| 2003/0054046 | A1 | 3/2003 | Burrell et al. | |
| 2003/0108608 | A1 | 6/2003 | Laridon et al. | |
| 2003/0113378 | A1 | 6/2003 | Laridon et al. | |
| 2003/0118624 | A1 | 6/2003 | Jackson et al. | |
| 2003/0118629 | A1 | 6/2003 | Scholz et al. | 424/443 |
| 2003/0118733 | A1 | 6/2003 | Jackson et al. | |
| 2003/0149106 | A1 | 8/2003 | Mosbey et al. | 514/554 |
| 2003/0175503 | A1 | 9/2003 | Lucast et al. | 428/343 |
| 2003/0185889 | A1 * | 10/2003 | Yan et al. | 424/484 |
| 2003/0190851 | A1 | 10/2003 | Yan et al. | |
| 2004/0126433 | A1 | 7/2004 | Parsons et al. | |
| 2004/0180093 | A1 | 9/2004 | Burton et al. | 424/489 |
| 2004/0229034 | A1 | 11/2004 | Djokic | |
| 2005/0025794 | A1 | 2/2005 | Wang et al. | 424/401 |
| 2005/0123590 | A1 | 6/2005 | Burton et al. | |
| 2005/0123621 | A1 | 6/2005 | Burton et al. | |
| 2006/0034899 | A1 | 2/2006 | Ylitalo et al. | |
| 2006/0035039 | A1 | 2/2006 | Ylitalo et al. | |
| 2006/0051385 | A1 | 3/2006 | Scholz et al. | |
| 2006/0173087 | A1 | 8/2006 | Hyde et al. | |
| 2006/0233888 | A1 | 10/2006 | Burton et al. | |
| 2006/0233889 | A1 | 10/2006 | Burton et al. | |
| 2007/0166399 | A1 | 7/2007 | Burton et al. | |
| 2008/0279960 | A1 | 11/2008 | Burton et al. | |

FOREIGN PATENT DOCUMENTS

| | | | |
|---|---|---|---|
| CN | 1308102 | A * | 8/2001 |
| CN | 1169883 | C | 10/2004 |
| CN | 1322874 | C | 1/2005 |
| CN | 1605676 | | 4/2005 |
| DE | 2 260 536 | | 7/1974 |
| DE | 273 846 | A1 | 11/1989 |
| DE | 199 58 697 | A1 | 6/2001 |
| EP | 0 126 528 | A2 | 11/1984 |
| EP | 0 172 025 | B1 | 2/1986 |
| EP | 0 172 724 | A2 | 2/1986 |
| EP | 0 272 149 | A2 | 6/1988 |
| EP | 0 326 382 | B1 | 8/1989 |
| EP | 0 172 724 | B1 | 7/1991 |
| EP | 0 272 149 | B1 | 3/1992 |
| EP | 0 489 967 | A2 | 6/1992 |
| EP | 0 497 607 | B1 | 8/1992 |
| EP | 512855 | A2 * | 11/1992 |
| EP | 0 528 191 | A1 | 2/1993 |
| EP | 0 567 704 | B1 | 11/1993 |
| EP | 1 033 141 | A1 | 9/2000 |
| EP | 0 984 698 | B1 | 4/2003 |
| EP | 1 601 386 | B1 | 12/2006 |
| GB | 769799 | | 3/1957 |
| GB | 2 127 389 | A | 4/1984 |
| JP | 63077948 | | 4/1988 |
| JP | 02303818 | | 12/1990 |
| JP | 3-193047 | | 8/1991 |
| JP | 03193047 | | 8/1991 |
| JP | 4-272754 | | 9/1992 |
| JP | 4-272764 | | 9/1992 |
| JP | 4-272765 | | 9/1992 |
| JP | 2-684217 | | 12/1997 |
| TW | 443932 | | 7/2001 |
| WO | WO 84/01721 | | 5/1984 |
| WO | WO 89/02754 | A1 | 4/1989 |
| WO | WO 91/09633 | A1 | 7/1991 |
| WO | WO 96/11226 | A2 | 4/1996 |
| WO | WO 96/25469 | A1 | 8/1996 |
| WO | WO 97/00163 | A1 | 1/1997 |
| WO | WO 97/23577 | A1 | 7/1997 |
| WO | WO 98/41095 | A2 | 9/1998 |
| WO | WO 98/41095 | A3 | 9/1998 |
| WO | WO 99/15101 | A2 | 4/1999 |
| WO | WO 99/15101 | A3 | 4/1999 |
| WO | WO 99/57201 | A1 | 11/1999 |
| WO | WO 00/09173 | A1 | 2/2000 |
| WO | WO 2000/009173 | A1 | 2/2000 |
| WO | WO 00/71183 | A1 | 11/2000 |
| WO | WO 00/74916 | A1 | 12/2000 |
| WO | WO 01/24839 | A1 | 4/2001 |
| WO | WO 01/43549 | A2 | 6/2001 |
| WO | WO 01/43549 | A3 | 6/2001 |
| WO | WO 01/43788 | A2 | 6/2001 |
| WO | WO 02/18003 | A1 | 3/2002 |
| WO | WO 02/43743 | A1 | 6/2002 |
| WO | WO 02/066087 | A1 | 8/2002 |
| WO | WO 02/078755 | A2 | 10/2002 |
| WO | WO 02/078755 | A3 | 10/2002 |
| WO | WO 03/022317 | A1 | 3/2003 |
| WO | WO 03/047636 | A2 | 6/2003 |
| WO | WO 03/053484 | A1 | 7/2003 |
| WO | WO 03/080911 | A2 | 10/2003 |
| WO | WO 03/080911 | A3 | 10/2003 |
| WO | WO 2004/017738 | A1 | 3/2004 |
| WO | WO 2004/080498 | A1 | 9/2004 |
| WO | WO 2004/080499 | A1 | 9/2004 |
| WO | WO 2004/101014 | A2 | 11/2004 |
| WO | WO 2004/101014 | A3 | 11/2004 |

| | | | |
|---|---|---|---|
| WO | WO 2004/112850 A1 | 12/2004 |
| WO | WO 2005/038122 A1 | 4/2005 |
| WO | WO 2005/056067 A1 | 6/2005 |
| WO | WO 2005/056069 A1 | 6/2005 |
| WO | WO 2005/056070 A1 | 6/2005 |
| WO | WO 2006/113052 A2 | 10/2006 |
| WO | WO 2006/113052 A3 | 10/2006 |

OTHER PUBLICATIONS

Gibbins et al.; Clinical study entitled "An in-vitro Comparison of a New Antimicrobial Polyacrylate Absorbent Wound Dressing Containing Silver with the Silver-containing Antimicrobial Film Dressings" from AcryMed dated Oct. 1999 (7 pgs.) printed Sep. 27, 2001.

"Surgical Materials"; British Pharmacopoeia, 1993, Addendum 1996, pp. 1943-1944; HMSO London, England.

Calvert et al.; "Photochemistry"; Chapter II; John Wiley & Sons Inc. (1966) pp. 27-125.

Sheet entitled "Rheology Modifiers" from Ciba Specialty Chemicals 2001 (1 pg.).

Brochure entitled "Ciba® SALCARE® SC95—Rheology Modifier" from Ciba Specialty Chemicals 2001 (5 pgs.).

Tech Brief from NASA Tech Briefs entitled "Bayer Develops New Superabsorbent Polymers"; printed Oct. 2, 2001 (1 pg.).

Odian, G.; "Principles of Polymerization"; 3rd Edition; 1991; pgs. Table of Contents and 352-353.

Park et al.; "Preparation and Characterization of Water-Swellable Natural Rubbers"; Journal of Applied Polymer Science; vol. 80, 2001; pp. 115-121.

Hageman, H.J.; "Photoinitiators for Free Radical Polymerization"; Progress in Organic Coatings, 13 (1985) pp. 123-150.

Wente et al; "Manufacture of Superfine Organic Fibers"; Report No. 4364 of the Naval Research Laboratory, published May 25, 1954.

Wente; "Superfine Thermoplastic Fibers"; Industrial and Engineering Chemistry; vol. 48, No. 8, pp. 1342-1346; Aug. 1956.

Wright et al.; "The Comparative Efficacy of Two Antimicrobial Barrier Dressings: In vitro Examination of Two Controlled Release of Silver Dressings"; Wounds 10(6); 179-188, 1998 © Health Management Publications, Inc.

Linke et al "Argentum" *Solubilities of Inorganic and Metal-organic Compounds*, vol. I (*A-Ir*) and vol. II (*K-Z*); *A Compilation of Solubility Data from the Periodical Literature, 4$^{th}$ edition*. D. Van Nostrand Co, Inc.; Princeton New Jersey, 1958. Title page and pp. 50-51.

Nesbitt and Sandmann "Solubility Studies of Silver Sulfadiazine." 1977 *J. Pharm. Sci.* 66(4):519-522.

Weast *Handbook of Chemistry and Physics, 64$^{th}$ edition*; CRC Press 1983-1984; Cover page, publisher's page, table of contents, and p. B-137.

Acel, "Concerning the Oligodynamic Effect of Metals;" 1920 *Biochemical Magazine* pp. 23-26. (English language translation included.).

Grier; "Silver and Its Compound"; Disinfection, Sterilization and Preservation (3$^{rd}$ Ed.) Ch. 18 , pp. 375-389.

Antelman "Silver (II, III) Disinfectants." Soap/Cosmetics/Chemical Specialties. Mar. 1994. pp. 52-59.

Applied Polymer Science. Craver (Ed.) et al. Organic Coatings and Plastics Chemistry. ACS 1975: Library of Congress Catalog Control No. 75-23010. 7 pgs.

CRC Handbook of Polymer-Liquid Interaction Parameters and Solubility Parameters. Second Edition. A.F.M. Barton: Boca Raton, FL; 1990. 4 pgs.

Furr et al. "Antibacterial Activity of Actisorb Plus, Actisorb and Silver Nitrate." 1994 *J. Hosp. Infect*. 27:201-208.

Grulke "Solubility Parameter Values." Polymer Handbook, Third Edition. Brandrup and Immergut (Eds.). John Wiley Publishers: New York, NY; 1989: 519-559.

Nomiya et al. "Syntheses, Crystal Structures and Antimicrobial Activities of Polymeric Silver(1) Complexes with Three Amino-Acids [aspartic acid ($H_2$asp), Glycine (Hgly) and Asparagine (Hasn)]." 2002 *J. Chem. Soc. Dalton Trns*. pp. 2483-2490.

Russell et al.; "Antimicrobial Activity and Action of Silver"; Progress in Medicinal Chemistry; vol. 31; 1994; pp. 351-370.

Thomas et al. "A Comparison of the Antimicrobial Effects of Four Silver-Containing Dressings on Three Organisms." 2003 *J. Wound Care* 12(3):101-107.

Tredget et al. "A Matched-Pair, Randomized Study Evaluating the Efficacy and Safety of Acticoat* Silver-Coated Dressing for the Treatment of Burn Wounds." 1998 *J. Burn Care and Rehab*. 19(6):531-537.

VanKrevelen (Ed.) Properties of Polymers, Third Edition. Elsevier Science: New York, NY; 1990. 8 pgs.

Wright et al. "Wound Management in an Era of Increasing Bacterial Antibiotic Resistance: A Role for Topical Silver Treatment." 1998 *AJIC* 26(6):572-577.

"Adhesives," *British Pharmacopoeia*, Appendix XX H. 1988, H.M. S.O. London: A222-A223.

Mahdavi et al., "Preparation and evaluation of cosmetic patches containing lactic and glycolic acids," *Indian Journal of Dermatology. Venerology and Leprology*, Nov.-Dec. 2006;72(6):432-436.

"Sheetable Polyester Label Material" datasheet [online]. 3M, St. Paul, MN , Jan. 1, 1999. [retrieved on Sep. 4, 2008]. Retrieved from the Internet:<URL:http://www.safetylabel.com/pdfs/3m7908.pdf>; 4 pgs.

Wokovich et al., "Evaluation of substrates for 90 degree peel adhesion- A collaborative study. I. Medical Tapes," *J. Biomed Mater Research Part B: Appl Biomater*, Published. online Apr. 3, 2008. Retrieved from the internet of Aug. 6, 2008 from http://www.3.interscience.wiley.com/cgi-bin/fulltext/119818079/main.html,ftx_abs (6 pgs.).

* cited by examiner

POLYMER COMPOSITIONS WITH BIOACTIVE AGENT, MEDICAL ARTICLES, AND METHODS

BACKGROUND

Polymer compositions that include bioactive agents (e.g., antimicrobial agents) are used for a variety of applications, particularly medical applications such as wound dressings and wound packing materials. Conventional antimicrobial agents include ionizable silver compounds (e.g., silver salts such as silver nitrate); however, they are typically not light stable and leave a stain on skin with which they come into contact. Thus, stable antimicrobial polymer compositions are desired.

SUMMARY

The present invention is directed to polymer compositions, and methods of making and using them, that include a sparingly soluble silver compound, a copper compound, a zinc compound, or combinations thereof. Of these, it is more typically a silver compound. Such compositions are useful in medical articles, particularly wound dressings, wound packing materials, topical creams, and topical lotions, although a wide variety of other products can incorporate the polymer compositions. Such compositions are preferably stable. By this it is meant that the compositions are stable to at least one of the following types of radiation: visible light, ultraviolet light, electron beam, and gamma ray sterilization.

In one embodiment, the polymer composition comprises a hydrophilic polymer and a bioactive agent selected from the group consisting of a metal oxide of silver, copper, zinc, and combinations thereof. The bioactive agent has a particle size less than one micron and is dispersed within the hydrophilic polymer.

In certain embodiments, the hydrophilic polymer is an amine-containing organic polymer selected from the group consisting of poly(quaternary amines), polylactams, polyamides, and combinations thereof. In certain embodiments, the hydrophilic polymer is a carboxylic acid-containing organic polymer.

In another embodiment, the polymer composition is preparable by a method comprising combining the hydrophilic polymer; a metal compound selected from the group consisting of a silver compound, a copper compound, a zinc compound, and combinations thereof, wherein the silver compound has a solubility of at least 0.1 gram per liter in water; and a hydroxide source that converts the metal compound to the corresponding metal oxide. The components are combined in a manner to disperse the metal oxide within the hydrophilic polymer.

In another embodiment, the polymer composition is preparable by a method comprising combining the hydrophilic polymer; an ammonia source; a metal oxide selected from the group consisting of silver oxides, copper oxides, zinc oxide, and combinations thereof. The metal oxide dispersed within the hydrophilic polymer has a particle size less than one micron. The ammonia source can be ammonia and/or ammonium salts. When combined, the ammonia and metal oxide form an ammonia-metal complex with a solubility greater than 0.1 gram per liter in water.

In one embodiment, the polymer composition is preparable by a method comprising combining a dispersion comprising absorbent hydrophilic microparticles; a metal compound selected from the group consisting of a silver compound, a copper compound, a zinc compound, and combinations thereof, wherein the silver compound has a solubility of at least 0.1 gram per liter in water; and a hydroxide source that converts the metal compound to the corresponding metal oxide. The components are combined in a manner to incorporate the metal oxide within the microparticles. The microparticles when in a substantially nonhydrated form have an average particle size of 10 microns or less.

In another embodiment, a polymer composition is preparable by a method comprising combining an organic polymer matrix; a dispersion comprising absorbent hydrophilic microparticles; a metal compound selected from the group consisting of a silver compound, a copper compound, a zinc compound, and combinations thereof, wherein the silver compound has a solubility of at least 0.1 gram per liter of water; and a hydroxide source that converts the metal compound to the corresponding metal oxide. The metal oxide is incorporated within the microparticles. The organic polymer matrix preferably comprises a hydrophobic polymer.

In another embodiment, the hydrophilic polymer is an amine-containing polymer selected from the group consisting of poly(quaternary amines), polylactams, polyamides, and combinations thereof.

Preferably, the polymer composition optionally includes a second organic polymer, thereby forming a mixture or blend of polymers. The second organic polymer is preferably a hydrophobic material. In one embodiment, the hydrophobic material forms a continuous matrix and the hydrophilic polymer forms a discontinuous phase (e.g., microparticles). In another embodiment, the hydrophobic material forms a discontinuous phase and the hydrophilic polymer forms a continuous matrix. In still another embodiment, the hydrophobic material forms a bi-continuous or co-continuous phase with the hydrophilic amine-containing polymer.

In another aspect, methods of making the polymer compositions are also provided. In one embodiment, the method comprises combining a dispersion comprising hydrophilic organic microparticles with water and a metal compound under conditions effective to distribute substantially all of the metal compound in the hydrophilic organic microparticles, wherein the metal compound is selected from the group consisting of a silver compound with a solubility of at least 0.1 gram per liter in water, a copper compound, a zinc compound, and combinations thereof; adding a hydroxide source to convert the metal compound to the corresponding metal oxide; optionally adding a secondary organic polymer to the dispersion; and optionally removing a substantial portion of the water. The method can also include combining an oxidizing agent to form a higher valence metal oxide.

In another embodiment, the method comprises combining monomers for a hydrophilic organic polymer with a metal compound under conditions effective to polymerize the monomers and distribute substantially all of the metal compound within the hydrophilic organic polymer, wherein the metal compound is selected from the group consisting of a silver compound with a solubility of at least 0.1 gram per liter in water, a copper compound, a zinc compound, and combinations thereof; adding a hydroxide source to convert the metal compound to the corresponding metal oxide; and optionally adding a secondary organic polymer to the hydrophilic organic polymer.

In another embodiment, the method comprises combining a hydrophilic polymer; an ammonia source; and a metal oxide selected from the group consisting of silver oxides, copper oxides, zinc oxide, and combinations thereof. The metal oxide dispersed within the hydrophilic polymer has a particle size of less than one micron.

The present invention also provides medical articles that include the polymer compositions. The medical articles can be any of a wide variety of products, but preferably are wound dressings, wound packing materials, topical creams, or topical lotions.

In certain embodiments, the present invention provides a wound dressing that includes an apertured liquid permeable substrate and a nonadherent composition of the present invention.

As used herein, "a," "an," "the," "at least one," and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

As used herein, "solubility" is presumed to be solubility in water at room temperature, typically 23° C.

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS OF THE INVENTION

The present invention provides polymer compositions that include a hydrophilic polymer, an optional second organic polymer, and a bioactive agent dispersed therein. The polymer composition can be in a wide variety of forms, such as an extruded film (e.g., having a thickness of 0.5 millimeter (mm) to 10 mm), a coating, a foam, particles, a hydrocolloid (i.e., a material that contains particles dispersed in a second phase, typically, hydrophilic particles dispersed in a lipophilic phase), a gel, a lotion, a cream, a molded article, etc.

In certain embodiments, the hydrophilic polymer is an amine-containing polymer selected from the group consisting of poly(quaternary amines), polylactams, polyamides, and combinations thereof. In certain embodiments, the hydrophilic polymer is a carboxylic acid-containing organic polymer. In certain embodiments, the hydrophilic polymer is in the form of microparticles. The second organic polymer in certain embodiments forms a continuous matrix, and in certain embodiments is a hydrophobic material.

The bioactive agent is typically a metal compound selected from the group consisting of a silver compound, a copper compound, a zinc compound, and combinations thereof. Of these, it is more typically a silver compound. In certain embodiments, the polymer composition is preparable from a dispersion that includes absorbent hydrophilic microparticles. In other embodiments, the polymer composition further comprises an organic polymer matrix.

The compositions of the present invention are preferably stable. By this it is meant that the compositions are stable to at least one of the following types of radiation: visible light, ultraviolet light, electron beam, and gamma ray sterilization. Such compositions are useful in medical articles, particularly wound dressings, wound packing materials, topical creams, and topical lotions, although a wide variety of other products can incorporate the polymer compositions. The wound dressings can be used in their hydrated or swollen forms if desired.

In certain embodiments, the compositions of the present invention are nonadherent, although it should be understood that an adhesive (e.g., a pressure sensitive adhesive) could be added to an article that includes the composition. As used herein, the nonadherent compositions of the present invention coated on a substrate display a 180° peel strength of less than 1 N/cm from steel according the to test procedure described in the Examples Section. Preferably, the compositions of the present invention do not adhere significantly to wound tissue such that they do not cause pain and/or destruction of the wound tissue upon removal.

Hydrophilic Polymers

The hydrophilic polymers can include anionic, cationic, amphoteric, non-ionic polymers, or combinations thereof. Typically, the type and amount of polymers are selected to provide the desired absorbency to the polymer composition of the present invention.

Preferably, the hydrophilic polymer has a weight average molecular weight of at least 1000. Preferably, the polymer is also dermatologically acceptable and non-reactive with the skin of the patient or with other components of the composition including any antimicrobial agents that may be present in therein.

Hydrophilic polymers (i.e., having an affinity for, absorbing, wetting smoothly with, tendency to combine with, or capable of dissolving in water) useful in the present invention may be made from a wide variety of synthetically prepared polymers, naturally occurring polymers, or chemically modified naturally occurring hydrophilic polymers. Varieties of polymers that can be used include synthetic polymers prepared from single or multiple monomers. The hydrophilic polymers can be in a dispersion, such as a dispersion that includes absorbent hydrophilic microparticles.

Non-limiting examples of such polymers include: polyhydroxyalkyl acrylates and methacrylates (e.g., those prepared from 2-hydroxyethyl acrylate, 2-hydroxyethyl methacrylate, 2-hydroxypropyl acrylate, 2-hydroxypropyl methacrylate, 2,3-dihydroxypropyl methacrylate); poly(meth)acrylic acid and salts thereof (wherein (meth)acrylic acid refers to methacrylic acid and acrylic acid); polyvinyl lactams (e.g., those prepared from N-vinyl lactams such as N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam); polyvinyl alcohols; polyoxyalkylenes; polyacrylamides; polystyrene sulfonates, natural or synthetically modified polysaccharides (e.g., starch, glycogen, hemicelluloses, pentosans, gelatin, celluloses, pectin, chitosan, and chitin), alginates, gums (e.g., Locust Bean, Guar, Agar, Carrageenan, Xanthan, Karaya, alginates, tragacanth, Ghatti, and Furcelleran gums), cellulosics (e.g., those prepared from methyl cellulose, hydroxypropyl methyl cellulose, carboxymethylcellulose and its salts, and hydroxypropyl cellulose); polymers prepared from water soluble amides (e.g., N-(hydroxymethyl)acrylamide and N-methacrylamide, N-(3-hydroxpropyl)acrylamide, N-(2-hydroxyethyl)methacrylamide, N-(1,1-dimethyl-3-oxabutyl)acrylamide N-[2-(dimethylamine)ethylacrylamide and -methacrylamide, N-[3-(dimethylamino)-2-hydroxylpropyllmethacrylamide, and N-[1,1-dimethyl-2-(hydroxymethyl)-3-oxabutyllacrylamide)); polymers prepared from water-soluble hydrazine derivatives (e.g., trialkylamine methacrylimide, and dimethyl-(2-hydroxypropyl)amine methacrylimide); mono-olefinic sulfonic acids and their salts, (such as sodium ethylene sulfonate, sodium styrene sulfonate and 2-acrylamideo-2-methylpropanesulfonic acid)). Other polymers include those prepared from the following monomers containing nitrogen in the non-cyclic or cyclic backbone of the monomer: 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylyl-morpholine.

For certain embodiments, the hydrophilic polymers are prepared with amine-containing organic polymers. The amine-containing organic polymers include poly(quaternary amines), polylactams, polyamides, and combinations thereof (including blends, mixtures, or copolymers thereof).

Preferably, the amine-containing polymer has a weight average molecular weight of at least 1000. Examples include, but are not limited to, polyvinyl pyrrolidone, polyvinyl caprolactam, poly-N-vinylacetamide, poly-N-vinyl formamide, polyacrylamide, and the like.

Preferably, the amine-containing organic polymer includes a quaternary amine, and more preferably, the amine-containing polymer is a quaternary ammonium salt of an organic polymer. Such polymers are preferred typically because they can stabilize the bioactive compounds (particularly, silver compounds) effectively, they provide good release of the bioactive compounds, and they are absorbing of water or bodily fluids (e.g., wound exudate). Examples include, but are not limited to, polymerization products of cationic vinyl monomers as disclosed in EP 0 489 967 A1, and inherently antimicrobial quaternary amine polymers as described in U.S. Pat. No. 6,039,940.

Other suitable amine-containing polymers can be prepared from a quaternary ammonium monomer, which is a salt having an organo-ammonium group and a monoethylenically unsaturated group. For certain embodiments, the quaternary ammonium monomer has the following general Formula (I):

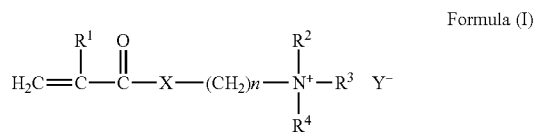

Formula (I)

wherein: n is 2 to 10, preferably 2 to 3; $R^1$ is H or $CH_3$; $R^2$, $R^3$, and $R^4$ are each independently linear or branched organic groups, preferably having 1 to 16 carbon atoms (on average); X is O or NH; and $Y^-$ is an acceptable anionic counterion to the $N^+$ of the quaternary ammonium group (e.g., one that does not adversely affect the polymerization of the monomers or antimicrobial activity of an added antimicrobial agent).

Preferably, $R^2$, $R^3$, and $R^4$ are each independently alkyl, aryl, alkaryl, or aralkyl groups. Alkyl groups are preferably lower alkyl, having 1 to 16 carbon atoms (on average) with methyl and ethyl groups being particularly preferred. Aryl is preferably phenyl but can be any suitable aromatic moiety such as those selected from the group consisting of phenyl, thiophenyl, naphthyl, biphenyl, pyridyl, pyrimidinyl, pyrazyl, pyridazinyl, furyl, thienyl, pyrryl, quinolinyl, bipyridyl, and the like. Representative of an aralkyl grouping is benzyl and representative of an alkaryl grouping is tolyl. X is preferably O. Representative counterions ($Y^-$) are $Cl^-$, $Br^-$, $HSO_4^-$, $CH_3CH_2OSO_3^-$, and $CH_3OSO_3^-$, with the chloride salts being particularly preferred. Alkyl groups can be straight or branched chain and alkyl and aryl groups can be substituted by non-interfering substituents that do not obstruct with the functionality of the polymers.

Useful copolymerizable quaternary ammonium monomers include, but are not limited to, those selected from 2-(meth) acryloxyethyl trialkyl ammonium halides and sulfates, and mixtures thereof. Examples of such compounds include, but are not limited to, 2-(meth)acryloxyethyl trimethyl ammonium chloride, $CH_2$=$C(H$ or $CH_3)CO_2CH_2CH_2N(CH_3)_3Cl$; 2-(meth)acryloxyethyl trimethyl ammonium methyl sulfate, $CH_2$=$C(H$ or $CH_3)CO_2CH_2CH_2N(CH_3)_3OSO_2OCH_3$; 2-(meth)acryloxyethyl methyl diethyl ammonium methyl sulfate, $CH_2$=$C(H$ or $CH_3)CO_2CH_2CH_2N(CH_3)(C_2H_5)_2$ $OSO_2OCH_3$; 2-(meth)acryloxyethyl dimethyl benzyl ammonium chloride, $CH_2$=$C(H$ or $CH_3)CO_2CH_2CH_2N(CH_3)_2$ $(C_6H_5CH_2)Cl$ (all of the preceding monomers available from Ciba Specialty Chemicals, Woodbridge, N.J.); 2-(methylacryloxy)ethyl dimethyl hexadecyl ammonium bromide, $CH_2$=$C(CH_3)CO_2CH_2CH_2N(CH_3)_2(C_{16}H_{33})Br$ (described in U.S. Pat. No. 5,437,932 (Ali et al.)); and the like. Various combinations of these monomers can be used if desired.

Due to their availability, effectiveness in reinforcing (meth)acrylate polymers, and their antimicrobial activity, particularly preferred quaternary ammonium monomers are 2-acryloxyethyl trimethyl ammonium methyl chloride and 2-acryloxyethyl methyl diethyl ammonium methyl chloride. Such monomers are typically hydrophilic. Various combinations of other monoethylenically unsaturated monomers that are reinforcing monomers can be used in the polymers of the present invention. Such reinforcing monomers include, but are not limited to, acrylic acid, methacrylic acid, ethylene vinyl acetate, and N,N-dimethylacrylamide.

As an alternative approach to providing polymers that contain a quaternary ammonium functional unit, it is possible to start with an amine monomer and form the quaternary ammonium unit following polymerization. For certain embodiments, the amine monomers have the following general Formula (II):

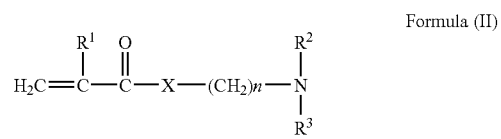

Formula (II)

wherein n, $R^1$, $R^2$, $R^3$, and X are the same as defined for Formula (I).

For certain embodiments, the hydrophilic polymers are prepared from carboxylic acid-containing organic polymers. Examples of such polymers include sodium polyacrylate (i.e., a copolymer of sodium acrylate and acrylic acid) microparticles such as those commercially available under the trade designation SALCARE SC91 from Ciba Specialty Chemicals (High Point, N.C.).

For certain embodiments, the hydrophilic polymer is in the form of particles. If the hydrophilic polymer is in the form of particles, it is typically in the form of microparticles. Preferably, the microparticles, when in a substantially nonhydrated form, have an average particle size of 10 microns or less, and more preferably, 1 micron or less. Typically and preferably, the microparticles have an average particle size of 0.5 micron or more when in a substantially nonhydrated form. Preferred microparticles are as described in EP 172 724 A2 and EP 126 528 A2 made by reverse phase polymerization and have a dry particle size below 4 microns.

For certain embodiments, the hydrophilic polymer (which is preferably in the form of microparticles) is absorbent (e.g., capable of absorbing water or bodily fluids). More preferably, the hydrophilic polymer (which is preferably in the form of microparticles) is superabsorbent. In this context, "superabsorbent" means that the material will absorb at least 100% of its weight.

In certain embodiments, the hydrophilic polymer can be particles, preferably in the form of microparticles, in a dispersion. The hydrophilic particles are typically dispersed in a continuous hydrophobic phase.

One type of dispersion is provided as a continuous hydrophobic liquid phase (e.g., mineral oil) and hydrophilic polymer particles dispersed within the hydrophobic liquid phase. Suitable examples of such materials are described in EP 0 126 528 A2. Such a material is commercially available under the trade designation SALCARE from Ciba Specialty Chemicals (High Point, N.C.). Suitable examples include SALCARE SC95 and SC96 which include a cationic homopolymer of the methyl chloride quaternary salt of 2-(dimethylamino)ethyl methacrylate (CAS No. 26161-33-1). Other suitable examples include SALCARE SC91, a copolymer of sodium acrylate and acrylic acid.

Monomers can be polymerized using techniques such as solution polymerization, emulsion polymerization, bulk polymerization, suspension polymerization, and the like. In particular, emulsion polymerization and suspension polymerization are preferable because the molecular weight of the polymer becomes high; solution polymerization is preferable because the molecular weight distribution is comparatively narrow; and bulk polymerization is favorable because no solvent is used.

In such polymerizations, initiators can be used to generate free-radicals upon the application of activating energy such as those conventionally used in the polymerization of ethylenically unsaturated monomers. Included among useful free-radical initiators are the thermally activated initiators such as organic peroxides, organic hydroperoxides, and azo-compounds. Representative examples of such initiators include, but are not limited to, benzoyl peroxide, tertiary-butyl perbenzoate, diisopropyl peroxydicarbonate, cumene hydroperoxide, azobis(isobutyronitrile), and the like. Generally, the thermal initiators are typically used in amounts from 0.01 to 5 percent by weight of monomer.

The polymerization of the polymer may also be initiated by photoinitiators. Such photochemically activated initiators are well known and have been described in the polymerization art; e.g., Chapter II of "Photochemistry" by Calvert and Pitts, John Wiley and Sons (1966) and in *Progress in Organic Coatings,* 13, 123-150 (1985). Representative examples of such initiators include benzoin, benzoin methyl ether, benzoin isopropyl ether, benzoin isobutyl ether, and 2-hydroxy-2-methyl-1-phenyl-1-propane, benzildimethylketal and benzildiethylketal, 2-hydroxy-1-(4-(2-hydroxyethoxy)phenyl)-2-methyl-1-propanone. A presently preferred photoinitiator is 2-hydroxy-1-(4-(2-hydroxyethoxy)phenyl)-2-methyl-1-propanone. Generally, photoinitiators are used in amounts from 0.01 to 5 percent by weight of monomer.

The polymerization of the polymer may also be initiated by electromagnetic radiation such as electron beams and the gamma-rays of cobalt 60, and the like. The irradiation dose is typically between 1 and 100 kGy.

The polymer may be crosslinked by adding a crosslinking compound or through electron beam or gamma radiation. A crosslinking compound can be a multi-ethylenically unsaturated compound wherein the ethylenic groups are vinyl groups, allyl groups, and/or methallyl groups bonded to nitrogen or oxygen atoms. Exemplary compounds include divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas.

The hydrophilic polymers can be used in a variety of combinations. The total amount of hydrophilic polymer(s) (e.g., microparticles) is preferably at least 1 percent by weight (wt-%), and more preferably, at least 5 wt-%, based on the total weight of the polymer composition. The total amount of hydrophilic polymer(s) (e.g., microparticles) is preferably at most 60 percent by weight (wt-%), based on the total weight of the polymer composition.

Bioactive Agent

The polymer compositions of the present invention typically include a bioactive agent that is a metal compound selected from the group consisting of a silver compound, a copper compound, a zinc compound, and combinations thereof. When dispersed within the hydrophilic polymer, the silver, copper, and zinc compounds are typically in the form of metal oxides. The metal compounds are typically antimicrobial, although they can also demonstrate other activities, such as antifungal activity. Preferably, the bioactive agent is a silver compound.

Substantially all of the dispersed silver, zinc, and copper compounds have an average particle size less than 1 micron in size. By utilizing a process that solubilizes the metal compound, either through use of a soluble metal compound that is converted in-situ to the corresponding metal oxide with a hydroxide source, or by complexing the metal oxide using an ammonia source in situ, the resulting dispersed metal oxides form particles within the hydrophilic polymer. Average particles sizes less than 1 micron are provided in part by the tendency of the metal oxide to form a complex with the hydrophilic polymer. The small particle size allows accelerated dissolution based on the high surface area to mass ratio of the particle.

One or more bioactive agents of this type can be used. Herein, these are considered the primary bioactive agents. Optionally, one or more secondary bioactive agents (e.g., antimicrobial agents, antibiotics) can be used in combination with these primary bioactive agents. Preferred compositions have more than one bioactive agent.

The bioactive agent can be present in the polymer composition in an amount to produce a desired effect (e.g., antimicrobial effect). Preferably, the bioactive agent is present in an amount such that the polymer composition is stable. In this context, "stable" means the composition does not turn black over a typical exposure time in the presence of at least one of the following types of radiation: visible light, ultraviolet light, electron beam, and gamma ray sterilization.

A preferred molar ratio of the metal compound to hydrophilic monomers (for the embodiments that prepare the polymer in situ) is at least 1 mole metal compound to 500 moles hydrophilic monomer. Although there is essentially no upper limit, a preferred molar ratio is no more than 1 mole bioactive agent to 20 moles hydrophilic monomer.

A preferred weight ratio of the metal compound to hydrophilic polymers (for the embodiments that mix the metal compound with a previously prepared polymer) is at least 0.1 weight percent (more preferably at least 1 weight percent) metal compound based on the total weight of the hydrophilic polymer. Although there is essentially no upper limit, a preferred weight ratio is no more than 10 weight percent (more preferably no more than 8 weight percent) metal compound based on the total weight of the hydrophilic polymer.

Secondary Polymer

The polymer compositions can include one or more secondary organic polymers in addition to one or more hydrophilic polymers. These can be liquids or solids at room temperature. This secondary polymer can be hydrophobic or hydrophilic, although preferably it is hydrophobic (i.e., antagonistic to, shedding, tending not to combine with, or incapable of dissolving in water).

Examples of hydrophilic materials include, but are not limited to, polysaccharides, polyethers, polyurethanes, polyacrylates, cellulosics, and alginates.

Examples of hydrophobic materials include, but are not limited to, polyisobutylene, polyethylene-propylene rubber, polyethylene-propylene diene-modified (EPDM) rubber, polyisoprene, styrene-isoprene-styrene, styrene-butadiene-styrene, styrene-ethylene-propylene-styrene, and styrene-ethylene-butylene-styrene. Hydrophobic materials are particularly desirable for nonadherent compositions and articles. Particularly preferred hydrophobic materials include styrene-isoprene-styrene and styrene-ethylene-butylene-styrene, and even more preferred materials include styrene-isoprene-styrene.

The secondary polymer can be in the form of a continuous matrix (i.e., phase) or a discontinuous matrix (e.g., in the form of particles). It can form a bi-continuous or co-continuous phase with the primary hydrophilic polymer. The secondary organic polymer can be elastomeric, thermoplastic, or both.

Elastomeric polymers useful as optional secondary polymers in the invention are typically materials that form one phase at 21° C., have a glass transition temperature less than 0° C., and exhibit elastomeric properties. The elastomeric polymers include, but are not limited to, polyisoprenes, styrene-diene block copolymers, natural rubber, polyurethanes, polyether-block-amides, poly-alpha-olefins, (C1-C20) acrylic esters of (meth)acrylic acid, ethylene-octene copolymers, and combinations thereof.

Elastomeric materials useful in the present invention include, for example, natural rubbers such as CV-60 (a controlled viscosity grade natural rubber having Mooney viscosity of 60+/−5 ML, 1+4 at 100° C., available as an International commodity); butyl rubbers, such as Exxon Butyl 268 available from Exxon Chemical Co., Houston, Tex.; synthetic poly-isoprenes such as CARIFLEX IR309, available from Kraton Polymers, Houston, Tex., and NATSYN 2210, available from Goodyear Tire and Rubber Co., Akron, Ohio; ethylene-propylenes; polybutadienes; polyisobutylenes such as VISTANEX MM L-80, available from ExxonMobil Chemical Co.; and styrene-butadiene random copolymer rubbers such as AMERIPOL 1011A, available from BF Goodrich of Akron, Ohio.

Thermoplastic polymers useful as optional secondary polymers in the invention include, for example, polyolefins such as isotactic polypropylene; low density or linear low density polyethylene; medium density polyethylene; high density polyethylene; polybutylene; polyolefin copolymers or terpolymers, such as ethylene/propylene copolymer and blends thereof; ethylene-vinyl acetate copolymers such as ELVAX 260, available from E.I. DuPont de Nemours & Co., Wilmington, Del.; ethylene acrylic acid copolymers; ethylene methacrylic acid copolymers such as SURLYN 1702, available from E.I. DuPont de Nemours & Co.; polymethylmethacrylate; polystyrene; ethylene vinyl alcohol; polyester; amorphous polyester; polyamides; fluorinated thermoplastics such a polyvinylidene fluoride; polytetrafluoroethylene; fluorinated ethylene/propylene copolymers; halogenated thermoplastics such as a chlorinated polyethylene; and combinations thereof. Other exemplary thermoplastic polymers are disclosed in International Publication No. WO 97/23577.

Thermoplastic elastomeric polymers useful as optional secondary polymers in the invention are typically materials that form at least two phases at 21° C., flow at a temperature greater than 50° C. and exhibit elastomeric properties. Thermoplastic elastomeric materials useful in the present invention include, for example, linear, radial, star and tapered styrene-isoprene block copolymers such as KRATON D1107P, available from Kraton Polymers, and EUROPRENE SOL TE 9110, available from EniChem Elastomers Americas, Inc. Houston, Tex., linear styrene-(ethylene/butylene) block copolymers such as KRATON G1657 available from Kraton Polymers, linear styrene-(ethylene/propylene) block copolymers such as KRATON G1657X available from Kraton Polymers, styrene-isoprene-styrene block copolymers such as KRATON D1119P available from Kraton Polymers, linear, radial, and star styrene-butadiene block copolymers such as KRATON D1118X, available from Kraton Polymers, and EUROPRENE SOL TE 6205 available from EniChem Elastomers Americas, Inc., polyetheresters such as HYTREL G3548, available from E.I. DuPont de Nemours & Co., and poly-alpha-olefin based thermoplastic elastomeric materials such as those represented by the formula —($CH_2$—CHR) where R is an alkyl group containing 2 to 10 carbon atoms and poly-alpha-olefins based on metallocene catalysis such as ENGAGE EG8200, an ethylene/l-octene copolymer available from DuPont Dow Elastomers Co., Wilmington, Del. Other exemplary thermoplastic elastomers are disclosed in International Publication No. WO 96/25469.

Various combinations of secondary organic polymers in various amounts can be used to produce desired effects. This can be readily determined by one of skill in the art based on the teachings herein.

Optional Additives

The polymer compositions of the present invention can include a wide variety of optional additives. Examples include, but are not limited to, secondary bioactive agents, secondary absorbent particles, foaming agents, swelling agents, fillers, pigments, dyes, plasticizers (for example, mineral oil and petrolatum), tackifiers, crosslinking agents, stabilizers, compatibilizers, extruding aids, chain transfer agents, and combinations thereof.

In addition to the bioactive agents described above (e.g., silver, copper, and zinc compounds), other (secondary) bioactive agents can be incorporated into the polymer compositions of the present invention. Examples include, but are not limited to, antimicrobial agents such as parachlorometaxylenol, chlorhexidine and salts thereof, iodine, and iodophores, and antibiotics such as neomycin, bacitracin, and polymyxin B. Preferred compositions have more than one bioactive agent.

In certain embodiments, polymer compositions of the present invention can include secondary absorbent particles. Such secondary particles can be a particle with an average particle size of greater than 10 microns when in a substantially nonhydrated form. Preferably, such particles are superabsorbent. Examples include, but are not limited to, those described in U.S. Pat. No. 5,369,155.

In certain embodiments, polymer compositions of the present invention can include a swelling agent, preferably a nonvolatile swelling agent. Examples of swelling agents include, but are not limited to, polyols, monosaccharides, ether alcohols, and combinations thereof. Specific examples are disclosed in U.S. Pat. No. 5,270,358.

In certain embodiments, polymer compositions of the present invention can include fillers, which can be inorganic or organic. Examples of inorganic fillers include, but are not limited to, barytes, chalk, gypsum, kieserite, sodium carbonate, titanium dioxide, cerium oxide, silica dioxide, kaolin, carbon black, and hollow glass microbeads. Examples of organic fillers include, but are not limited to, powders based on polystyrene, polyvinyl chloride, urea-formaldehyde, and polyethylene. The fillers may be in the form of fibers, such as chopped fibers. Examples of suitable chopped fibers include glass fibers (typically 0.1 millimeter (mm) to 1 mm long) or fibers of organic origin such as, for example, polyester or polyamide fibers.

In order to confer color to the polymer compositions it is possible to use dyes or colored pigments of an organic or inorganic basis such as, for example, iron oxide or chromium oxide pigments or phthalocyanine- or monoazo-based pigments.

Methods of Preparation of Polymer Compositions and Articles

Whether starting with monomers and polymerizing the monomers in the presence of the bioactive agent, or adding a bioactive agent to a previously prepared polymer, the components are combined in a manner to produce a polymer composition having a bioactive agent dispersed therein.

The bioactive agent used to prepare the compositions of the present invention are chosen from silver compounds, zinc compounds and copper compounds, and combinations thereof. In one embodiment, at least the silver compound has a solubility in water of at least 0.1 gram per liter, and more preferably, the silver, copper, and zinc compounds each have a solubility in water of at least 0.1 gram per liter. Sufficient solubility, i.e., solubility of at least 0.1 gram per liter in water, is desirable such that the compounds are dissolved into the hydrophilic polymer phase. Examples of such metal compounds include, but are not limited to, silver nitrate, silver acetate, silver lactate, silver sulfate, copper chloride, copper nitrate, copper acetate, copper lactate, copper sulfate, zinc chloride, zinc nitrate, zinc acetate, zinc lactate, and zinc sulfate.

When using a metal compound soluble in the hydrophilic phase, a hydroxide source is added to convert the silver, zinc, and/or copper compound to the corresponding metal oxide. Suitable hydroxide sources include but are not limited to sodium hydroxide, potassium hydroxide, and calcium hydroxide. In preferred embodiments, and particularly those used in medical applications, the hydroxide source is sodium hydroxide.

In another embodiment, the metal compound has insufficient solubility, i.e., less than 0.1 g per liter of water, to allow dispersion of the metal compound in the hydrophilic polymer. Examples of such metal compounds include, but are not limited to, silver oxide, silver chloride, zinc oxide, copper oxide. In those instances, the metal compound is dissolved in ammonia or an ammonium compound, which forms a complex with the ammonia that is soluble in the hydrophilic phase. Suitable ammonia sources include ammonia, and ammonium salts such as ammonium pentaborate, ammonium acetate, ammonium carbonate, ammonium peroxyborate, ammonium terraborate, triammonium citrate, ammonium carbamate, ammonium bicarbonate, ammonium malate, ammonium nitrate, ammonium nitrite, ammonium succinate, ammonium sulfate, ammonium tartarate, and mixtures thereof.

In another embodiment, the metal compound with low solubility can be dissolved in a strong acid such as nitric acid or sulfuric acid. The metal compound forms a soluble salt that will disperse in the hydrophilic polymer. A neutralizing agent, such as sodium hydroxide or ammonium hydroxide, can be added to neutralize the strong acid.

In some embodiments, higher valence metal oxide, for example, where the oxidation state of silver is Ag(II), Ag(III), or Ag(IV), may be desired. The valence state of the metal oxide can be increased by the addition of an oxidizing agent. Suitable oxidizing agents include hydrogen peroxide and alkali metal persulfates such as sodium persulfate, as discussed in U.S. Pat. No. 6,436,420 to Antelman. Other suitable oxidizing agents include permanganates, hypochlorites, perchlorates, and nitric acid.

The components are combined in a manner to produce a polymer composition wherein the bioactive agent, i.e., the metal compound, is incorporated within the hydrophilic polymer. Preferably, this results from combining the components in the presence of water (e.g., 1-20 wt-%, based on the total weight of the composition) and then optionally removing a substantial portion of the water (such that less than 1 wt-% water is remaining, based on the total weight of the composition). If desired, all the water can be removed.

In certain embodiments, a dispersion that includes hydrophilic organic microparticles is combined with water, a metal compound, a hydroxide source, and optionally an oxidizing agent under conditions effective to disperse (preferably, dissolve) the metal compound in the hydrophilic organic microparticles. Optionally, a secondary organic polymer can be added to the mixture of the dispersion, water, hydroxide source and bioactive agent. Once sufficiently mixed to impregnate at least a portion of the bioactive agent (e.g., silver compound) into the hydrophilic particles, the water is removed if desired.

In certain embodiments, a dispersion that includes hydrophilic organic microparticles is combined with water, a metal compound with low solubility, i.e., less than 0.1 g per liter in water, an ammonia source, and optionally an oxidizing agent under conditions effective to disperse (preferably, dissolve) the metal agent in the hydrophilic organic microparticles. Optionally, a secondary organic polymer can be added to the mixture of the dispersion, water, ammonia source and metal compound with low solubility. Once sufficiently mixed to impregnate at least a portion of the insoluble bioactive agent (e.g., silver compound) into the hydrophilic particles, the ammonia is removed, and the water is removed if desired.

In other embodiments, monomers for a hydrophilic organic polymer are combined with a soluble form of the metal compound under conditions effective to polymerize the monomers and distribute (preferably dissolve) at least a portion of the metal in the hydrophilic organic polymer. The soluble form of the metal compound can be present during the polymerization process or added after the polymerization is complete. Once dispersed, the soluble form of the metal compound can be converted to the corresponding metal oxide. Optionally, a secondary organic polymer can be added to the hydrophilic organic polymer with the bioactive agent distributed therein.

The polymer compositions with the bioactive agent therein can be melt processed (e.g., extruded or molded) or solvent cast to form the desired products (e.g., wound dressing).

The materials used to prepare the polymer compositions of the present invention are melt processable if they are fluid or pumpable, and they do not significantly degrade or gel at the temperatures used to melt process (e.g., extruding or compounding) the composition (e.g., at least 50° C. and up to 300° C.). Preferably, such materials have a melt viscosity of at least 10 poise and often up to 1,000,000 poise, as measured by capillary melt rheometry at the processing temperatures and shear rates employed in extrusion. Typically, suitable materials possess a melt viscosity within this range at a temperature of at least 175° C. and often up to 225° C. and a shear rate of 100 seconds$^{-1}$.

Continuous melt process forming methods include drawing the extruded composition out of a film die and subsequently contacting a moving plastic web or other suitable backing. Another continuous forming method involves directly contacting the extruded composition to a rapidly moving plastic web or other suitable substrate. In this method, the extruded composition can be applied to a moving web using a die having flexible die lips such a reverse orifice coating die and other contact dies using rotating rods. The composition can also be extruded in the form of continuous fibers and blown micro-fiber webs as disclosed in Wente, Van A., "Superfine Thermoplastic Fibers," Industrial Engineering Chemistry, Vol. 48, pp. 1342-1346; Wente, Van A. et al., "Manufacture of Superfine Organic Fibers," Report No. 4364 of the Naval Research Laboratories, published May 25, 1954; U.S. Pat. No. 5,176,952 and U.S. Pat. No. 3,841,953. After melt process forming the composition is solidified by quenching using either direct methods, such as chill rolls or water baths, or indirect methods, such as air or gas impingement, or both.

In some embodiments, a non-adherent or adherent composition (which can be in the form of a gel) is preferably obtained by hot mixing without a solvent (so-called hot-melt process), by blending an elastomer with an oily plasticizer and antioxidants, and then by adding a hydrocolloid either as finely divided powder or as a dispersion. If active agents are provided, these may be added to either the elastomer or the hydrocolloid.

Articles can be prepared using compositions described herein according to a variety of methods, particularly coating methods. When a porous substrate is coated, the process of coating the porous substrate with the composition typically allows the yarns, filaments, or film to be properly trapped in the composition, while leaving most of the apertures unobstructed by the composition. Depending on the structure of the support used, the amount of composition employed will vary over a wide range (typically from 50 grams per square meter (g/m$^2$) to 300 g/m$^2$, and preferably from 60 g/m$^2$ to 160 g/m$^2$).

In certain embodiments, the coating can be carried out hot, without a solvent, using a continuous process in which the substrate is directed over a first coating roll covered with a layer of molten composition having a predetermined thickness, and then over a second roll which removes the composition lying within the apertures of the substrate. The substrate thus covered with gel only on the yarns, filaments, or film is then cooled in a stream of air so that the composition cannot flow and remains uniformly distributed around the yarns, filaments, or film. If necessary, a system producing a laminar stream of air is provided, which system is able both to correct the distribution of the composition around the yarns, filaments, or film and to unblock any substrate apertures, which would not have been open in the previous step of the process.

According to a variant of this process, a substrate can be passed through a bath of molten polymeric composition (for example, at a temperature of 120° C. to 200° C.). The substrate covered with molten composition is then passed between two fixed rolls pressed against each other with a predetermined gap, so as to remove the excess composition. The amount of composition remaining on the yarns, filaments, or film depends essentially on the gap set between the fixed rolls. The covered process is then cooled and treated in a manner similar to the previous process.

If desired, the cooled coated substrate can be covered with two protective films (for example, thin polyester films). These films may or may not require a nonstick treatment and can function to facilitate extraction from a package and in handling the article. If desired, the coated substrate can be cut into individual compresses, of sizes suitable for the use, packaged in sealed sachets, and sterilized.

Solvent casting may also be used to prepare the articles of the present invention. This method typically employs a common solvent, selected for compatibility with the polymer composition components. Such common solvents include, for example, toluene and tetrahydrofuran. Specific selection of a common solvent for a particular subset of the present invention is within the skill of the art. In the solvent casting method, the materials included in the composition are blended to form a uniform mixture, then coated onto a carrier web or a backing (described below) using a known coating technique such as gravure coating, curtain coating, die coating, knife coating, roll coating, or spray coating. A preferred coating method is knife coating. The solvent is then removed from the coated backing, usually with the aid of a drying oven for a time and temperature selected to remove any undesirable level of residual solvent.

In some embodiments, a composition containing a silver oxide can be coated on the polymer composition as described in applicants co-pending application Ser. No. 10/728,446, filed Dec. 5, 2003, incorporated herein by reference. The metal oxide is dissolved in solution by complexing the metal compound in an ammonium salt. Suitable ammonium salts include ammonium pentaborate, ammonium acetate, ammonium carbonate, ammonium peroxyborate, ammonium tetraborate, triammonium citrate, ammonium carbamate, ammonium bicarbonate, ammonium malate, ammonium nitrate, ammonium nitrite, ammonium succinate, ammonium sulfate, ammonium tartarate, and mixtures thereof. The resultant solution can be coated at less than 40° C., and dried at temperatures less than 160° C. Once dried, the substrate remains coated with the metal oxide.

In a preferred embodiment, the solution is formed from the combination of silver oxide and ammonium carbonate. The coated substrate is subsequently dried, optionally in the presence of heat. Ammonia and carbon dioxide are driven off, leaving essentially the silver oxide remaining on the substrate.

Layered constructions can also be prepared using lamination, coating, or extrusion techniques known to one of skill in the art and as described, for example, in U.S. Pat. No. 6,379,791.

If desired, compositions of the present invention can be sterilized. Methods of sterilization include treatment with electron beam or gamma radiation.

Medical Articles

The polymer compositions of the present invention can be used in a wide variety of products, although they are preferably used in medical articles. Such medical articles can be in the form of a wound dressing, wound packing material, or other material that is applied directly to or contacts a wound.

Such articles may or may not include a backing (i.e., a support substrate). If a backing or support substrate is desired, it can be porous or nonporous. The composition of the present invention can be coated on the support substrate or impregnated into it, for example.

Suitable materials are preferably flexible, and may be fabric, non-woven or woven polymeric films, metallic foils, paper, and/or combinations thereof. More specifically, film backings are useful with the polymer compositions of the present invention. For certain embodiments it is desirable to use a permeable (e.g., with respect to moisture vapor), open apertured substrate (i.e., a scrim). For certain embodiments it is desirable to use an open- or closed-cell foam, such as that disclosed in U.S. Pat. No. 6,548,727 to Swenson.

The substrates (i.e., backings) are preferably porous to allow the passage of wound fluids, moisture vapor, and air. In certain embodiments, the substrates are substantially impervious to liquid, especially wound exudate. In certain embodiments, the substrates are capable of absorbing liquid, especially wound exudate. In certain embodiments, the substrate is an apertured liquid permeable substrate.

Suitable porous substrates include knits, wovens (e.g., cheese cloth and gauze), nonwovens (including spun-bonded nonwovens), extruded porous sheets, and perforated sheets. The apertures (i.e., openings) in the porous substrates are of sufficient size and sufficient number to facilitate high breathability. For certain embodiments, the porous substrates have at least 1 aperture per square centimeter. For certain embodiments, the porous substrates have no greater than 225 apertures per square centimeter. For certain embodiments, the apertures have an average opening size (i.e., the largest dimension of the opening) of at least 0.1 millimeter (mm). For certain embodiments, the apertures have an average opening size (i.e., the largest dimension of the opening) of no greater than 0.5 cm.

For certain embodiments, the porous substrates have a basis weight of at least 5 grams/meter$^2$. For certain embodiments, the porous substrates have a basis weight of no greater than 200 grams/meter$^2$.

The porous substrates (i.e., backings) are preferably flexible yet resistant to tearing. For certain embodiments, the thickness of the porous substrates is at least 0.0125 mm. For certain embodiments, the thickness of the porous substrates is no greater than 3 mm.

Materials of the backing or support substrate include a wide variety of materials including paper, natural or synthetic fibers, threads and yarns made from materials such as cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, and/or combinations thereof.

The backing can also be provided with stretch-release properties. Stretch-release refers to the property of an adhesive article characterized in that, when the article is pulled from a surface, the article detaches from the surface without leaving significant visible residue. For example, a film backing can be formed from a highly extensible and highly elastic composition that includes elastomeric and thermoplastic A-B-A block copolymers, having a low rubber modulus, a lengthwise elongation to break of at least 200%, and a 50% rubber modulus of not above 2,000 pounds/square inch (13.8 megapascals (MPa)). Such backings are described in U.S. Pat. No. 4,024,312 (Korpman). Alternatively, the backing can be highly extensible and substantially non-recoverable such as those described in U.S. Pat. No. 5,516,581 (Kreckel et al.).

Pressure sensitive adhesives used in medical articles can be used in articles of the present invention. That is, a pressure sensitive adhesive material could be applied to the article of this invention, for example, around the periphery, to adhere the article to the skin.

In another aspect, the compositions of the present invention will be in the form of an aqueous gel. Suitable gelling agents include polyoxyethylene-polyoxypropylene diol block copolymers, polyacrylic acid lightly crosslinked with triallyl sucrose which has been neutralised using an alkali metal hydroxide, cellulosic derivatives such as carboxymethyl cellulose, hydroxymethyl cellulose, natural gums, and the like. It will be appreciated that care must be taken to avoid using gelling agents that are incompatible with the bioactive agent, such as the silver compounds. Suitable gel forming block copolymers of polyoxyethylene-polyoxypropylene will have a molecular weight from 4,600 to 13,500 (approximately) and will be present in the gel in an amount from 50% for the lower molecular weight copolymers to 20% for the higher molecular weight copolymers, so that the gel when applied topically is neither too stiff nor too fluid. Typically the gels are formed by mixing together the copolymer and water to form an aqueous solution at a temperature of 2° C. and adding the bioactive agent (e.g., silver compound) and then allowing the solution to gel as it warms to ambient temperature. A preferred group of gelling agents are the polyoxyethylene-polyoxypropylene diol block copolymers which are commercially available under the trade designation PLURONICS from BASF-Wyandotte (e.g., PLURONICS F108, F127, and P105).

EXAMPLES

Objects and advantages of this invention are further illustrated by the following examples, but the particular materials and amounts thereof recited in these examples, as well as other conditions and details, should not be construed to unduly limit this invention.

Materials

KRATON D4433—a pre-compounded KRATON D1112 and mineral oil (77/23) blend, where the KRATON D1112 is a linear polystyrene-polyisoprene-polystyrene (SIS) thermoplastic elastomeric copolymer having 15 wt. % polystyrene. The blend is available from Kraton Polymers, Houston, Tex.

KRATON D1124K—radial 4-arm star polystyrene-polyisoprene (SI)$_4$ thermoplastic elastomeric copolymer having 30 wt. % polystyrene available from Kraton Polymers, Houston, Tex.

KAYDOL—mineral oil available from Crompton Corporation, formerly Witco Corporation.

IRGANOX 1010—antioxidant available from Ciba Specialty Chemicals, Tarrytown, N.Y.

SALCARE SC91—50 wt-% solids cosmetic grade emulsion having micro-particles of chemically crosslinked hydrophilic anionic sodium acrylates copolymer in mineral and paraffin oils available from Ciba Specialty Chemicals, High Point, N.C.

SALCARE SC95—50 wt-% solids cosmetic grade emulsion having micro-particles of chemically crosslinked hydrophilic cationic quaternary ammonium acrylate polymer (methychloride quaternary ammonium salt of DMAEMA) in mineral and paraffin oils available from Ciba Specialty Chemicals, High Point, N.C.

Silver Nitrate (AgNO$_3$)—99+% reagent grade from Aldrich (Milwaukee, Wis.) was used to make a 5.6M AgNO3 solution by dissolving the as received AgNO3 in water. One hundred (100) grams of de-ionized (DI) water and 95.2 grams of silver nitrate were dissolved to make a 5.6 molar (M) silver nitrate solution Trypticase (Tryptic) Soy Broth (TSB)—medium available from Becton Dickinson & Company, Bedford, Mass.

Polyester Knitted Fabric was a 24 mesh polyester knit (61 g/m$^2$) purchased from Lamports Filter Media, Inc, Cleveland, Ohio.

10% Hydrogen Peroxide Solution was made by diluting 100 grams of a 30 wt. % hydrogen peroxide (H$_2$O$_2$—available from Mallinckrodt, St Louis, Mo.) with 200 grams of de-ionized water to make a 10 wt. % H$_2$O$_2$ solution 5.6 M NaOH solution was made by mixing 100 grams of DI water and 22.4 grams of sodium hydroxide to make a 5.6M NaOH solution.

Aqueous Silver (I) Oxide (Ag$_2$O) solution [1.3 wt. % Ag$_2$O, 4.4 wt. % (NH4)$_2$CO$_3$ and 94.3 wt. % water] made by mixing Ag$_2$O (Alfa Aesar, Ward Hill, Mass.) with ammonium carbonate solution until completely dissolved.

Ammonium carbonate, available from Mallinkrodt Baker, Inc., Phillipsburg, N.J.

Test Procedures

Antimicrobial Performance Tests

% Live Bacteria Test

The effectiveness of a sample was tested using a L-7012, Bacterial Viability Kit, available from Molecular Probes (Eugene, Oreg.). The procedure is outlined below using the red, propidium iodide dye, and green, SYTO 9 dye, contained in the kit to stain the live and dead bacteria.

Preparation of bacteria solution: *Staphylococcus aureus* bacteria were grown in Trypticase (Tryptic) Soy Broth (TSB) medium overnight. Bacteria were concentrated by centrifugation at 10,000× gravity for 15 minutes (min). Supernatant was removed and the pellet was re-suspended in MilliQ water (filtered through a 0.2 μm pore-size filter) or in Butterfield phosphate buffer (from Hardy Diagnostics, Santa Maria, Calif.). Bacteria solution was diluted to the desired bacteria concentration (10$^7$ cells/milliliters) by measuring the optical density (OD) at 670 nm. For a control experiment, the bacteria solution was incubated with 70% isopropyl alcohol at room temperature for 1 hour (hr) to measure the killed bacteria control. Different volume of live and dead bacteria solutions were mixed to generate a range of percent live solution for calibration purposes.

Bacteria labeling and Antimicrobial testing: 7 mls of bacteria solution at initial concentration of approximately 1×10$^8$ bacteria/mls were pipetted into a 50 mls conical tube containing the sample. At the specified time (e.g., 2 hr), 50 micro-liter (μL) of the supernatant was pipetted into fluorescent measurement tube which already contained 450 μL of MiliQ water and premixed green dye and red dye solution (1.5 μL dye mixture for 500 μL bacteria solution) was added and the mixture was incubated for 15 minutes in the dark at room temperature. These solutions were then measured by flow cytometry. Cell viability was measured using the BD FACS Caliber flow cytometer (made by Becton Dickinson & Company, Franidin Lakes, N.J.). The flow cytometer is equipped with an argon-ion laser at 488 nanometers (nm) and 15 milliWatts (mW) output. Data acquisition and analysis were controlled using CellQuest software and PBPAC hardware interface. The light path contained a 488/10 nm blocking filter, then a 530/30 nm filter before the green PMT and a 585/42 nm long pass filter before the red PMT. The sampling rate was around 3000-7000 particles/second. The sheath fluid was FACSFlow by Becton Dickinson. The instrument voltage was 5.5 Volt.

The live cell and dead bacteria responses were established with the 100% live cell and 100% dead cell (for killed bacteria, bacteria solution was incubated with 70% isopropyl alcohol at room temperature for 1 hr) samples. Different volumes of live and dead bacteria solutions were mixed to generate a range of percent live solutions for calibration purposes. The sample results for bacteria killing ability were interpolated from the standard curve generated from calibration samples. Total bacteria concentration was determined by the measuring of the OD at 670 nm of the bacteria solution.

Zone of Inhibition Test

Antimicrobial performance was measured using a Zone of Inhibition test (ZOI) that was performed by the following method. Mueller-Hinton agar was prepared, sterilized and tempered in a water bath at 48-50° C. A suspension of bacteria in sterile phosphate-buffered water was prepared with approximately 10$^8$ CFU/ml. The agar was inoculated with the bacterial suspension to an approximate concentration of 10$^5$ CFU/ml (1:1000). The inoculated agar was swirled to mix and pipetted (~14 ml) into sterile Petri dishes (15×100 rein). The seeded agar was allowed to set for about 20 minutes to harden. An alcohol-disinfected die and cutting board were used to cut textile samples to desired size. Sterile forceps were used to place the samples onto the seeded, hardened agar in center of plate. The plate was then placed into an incubator at 35-37° C. for overnight (16-24 hours) incubation. After incubation the clear zones, no visible colonies formed, were measured in mm with calipers.

The zone of inhibition (ZOI) is then calculated by the following equation $$ZOI=[\text{diameter of clear zone(mm)}-\text{diameter of sample (mm)}]/2$$

Saline Absorbency Test

Samples (2.54 cm by 2.54 cm) were soaked in saline. The samples were removed from the saline at various times and were lightly dabbed with a paper towel. The weight was recorded and the samples were placed back into the saline solution. The weight of saline absorbed per weight of dry coating was calculated as a function of swelling time in the saline using the following equation: (weight saline absorbed)/(dry coating sample weight)=[(saline swollen weight)−(dry sample weight)]/[(dry sample weight)−(weight of substrate)].

Peel Adhesion Test

Peel adhesion is measured as 180° peel from steel plates, at 23° C., 50% RH, 305 mm/min, 25 mm wide using a Model 3M90 Slip/Peel tester (IMASS, Inc., Accord, Mass.). The samples were conditioned for 24 hours at controlled temperature and humidity. After conditioning the samples were adhered to a stainless steel panel using 2 kg roller and 4 passes. The samples were peeled from the stainless steel plate after 15 minutes of dwell time using a 0.305 meter/minute peel rate. Typically two 0.13 m long samples were measured and the average peel force recorded in ounces/inch (oz/in) and converted to Newtons per centimeter (N/cm).

Preparation of Examples

Examples 1-3 were prepared by first preparing a gel as described below and combining that with a lot of silver modified SALCARE that was prepared as outlined below.

Preparation of Gel

Three lots of Styrene-isoprene-styrene (SIS) gel were prepared in the following manner. Lots 1 and used KRATON D4433-16 and Lot 3 used KRATON D1124 as the SIS pellets. SIS pellets were gravimetrically fed into the feed throat (barrel 1) of a Werner Pfleiderer ZSK30 co-rotating twin-screw extruder (TSE) having a 30 mm diameter barrel and 15 barrel sections. Each temperature zone was a combination of two barrel sections (e.g., Zone 1 corresponded to barrel sections 2 and 3). Barrel section 1 was controlled at full cooling capacity for all SIS gel lots. A powdered antioxidant (IRGANOX 1010) was also gravimetrically fed into barrel section 1 for SIS gel lot 3. KAYDOL mineral oil was heated and added to the TSE as described in publication WO97/00163. The disclosed compounding process provides a method for making a gel by melting of the SIS elastomer followed by addition of the heated mineral oil. Heated mineral oil was sequentially injected into barrel sections 4, 6, 8, 10 and 12, respectively. The TSE screw speed for lots 1-3 was controlled to 400 rpm. The TSE temperature profile for lot 1 and 2 was controlled to 204° C., 204° C., 204° C., 191° C., 177° C., 149° C. and 149° C. for zones 1-7, respectively. The heated oil injections for lot 1 were controlled to 204° C., 204° C., 177° C., 149° C. and 149° C. respectively. The TSE temperature profile for lot 3 was controlled to 204° C., 227° C., 227° C., 204° C., 182° C., 171° C. and 93° C. for zones 1-7, respectively. The heated oil injections for lot 3 were controlled to 204° C., 204° C., 204° C., 177° C. and 177° C. respectively. Table 1 contains the material flow rates and Table 2 contains the compositional information for SIS gel lots 1-3.

TABLE 1

SIS gel lot flow rates

| SIS Gel Lot# | SIS (g/min) | Barrel Section(S) and Oil addition # and Rate (g/min) | | | | | Total KAYDOL Oil (g/min) | IRGANOX 1010 (g/min) | Total Flow Rate (g/min) |
|---|---|---|---|---|---|---|---|---|---|
| | | S4 Oil 1 | S6 Oil 2 | S8 Oil 3 | S10 Oil 4 | S12 Oil 5 | | | |
| 1 | 125 | 41 | 55 | 64 | 50 | 50 | 260 | — | 385 |
| 2 | 125 | 41 | 55 | 40 | 30 | 30 | 196 | — | 321 |
| 3 | 227 | 74 | 100 | 120 | 120 | 108 | 522 | 8 | 757 |

TABLE 2

SIS gel lots 1-2 compositions

| SIS Gel Lot# | SIS Type | SIS (wt. %) | KAYDOL oil (wt. %) | IRGANOX 1010 (wt. %) | Total SIS Elastomer (wt. %) |
|---|---|---|---|---|---|
| 1 | linear | 32.5 | 67.5 | — | 25.0 |
| 2 | linear | 39.0 | 61.0 | — | 30.0 |
| 3 | radial | 30.0 | 69.0 | 1.0 | 30.0 |

Preparation of the Particles

Three lots of silver nitrate dispersed in SALCARE SC95 were prepared. Lot 1 was prepared by mixing 100 grams of SC95 with 2 milliliters (mls) of 5.6 molar (M) silver nitrate at a high speed using a 2 inch (5.08 cm) diameter, three-blade stainless steel paddle mixer. The silver nitrate solution was added drop wise such that all of the solution was added over ten minutes. After all of the silver nitrate solution was added the mixture was further mixed for another ten minutes. Sodium hydroxide solution (5.6 M, 1.0 ml) was then added over 10 minutes and all the ingredients mixed for another 10 minutes. Lot 2 and 3 were prepared in a similar manner as Lot 1 except twice as much silver nitrate solution was added for Lot 3 and more sodium hydroxide was added, 1.8 ml for Lot 2 and 3.0 ml for Lot 3. Lot 3 was also dehydrated in a Ross mixer operating at 60° C., 11 hertz and 28 inches of mercury vacuum for 6 hours. Table 3 contains the compositional information for SALCARE SC95/AgNO$_3$ lots 1-3.

TABLE 3

SALCARE SC95/AgNO$_3$ lots 1-3 compositions

| SALCARE SC95 Lot# | SALCARE SC95 (grams) | 5.6M AgNO$_3$ (mls) | 5.6M NaOH (mls) | DI H2O (wt. %) | AgNO$_3$/NaOH Molar ratio |
|---|---|---|---|---|---|
| 1 | 100.0 | 2.0 | 1.0 | 2.8 | 1/0.5 |
| 2 | 100.0 | 2.0 | 1.8 | 3.6 | 1/0.9 |
| 3 | 100.0 | 4.0 | 3.0 | Dehydrated | 1/0.75 |

Preparation of Examples 1-3

Examples 1-3 were prepared by combining pre-compounded SIS gel lots 1-3 with pre-compounded SALCARE SC95/AgNO$_3$ lots 1-3 in a Haake 25 mm diameter, fully intermeshing counter-rotating TSE. Example 1 was prepared by re-melting SIS gel lot 1 in a Bonnot extruder operating at 127° C. The molten gel was injected at 22.8 grams per minute into barrel section 1 of the TSE. SALCARE SC95 lot 1 was injected at ambient temperature into barrel section 3 at 15.2 grams per minute using a Zenith gear pump. The TSE was controlled at 300 rpm screw speed and 149° C. temperature. The total material throughput was 38.0 grams per minute for all Examples. The SIS gel/SALCARE blend was discharged out of the TSE into a transport hose using a Zenith gear pump. The transport hose conveyed the molten gel blend to a 0.15 meter (m) wide single orifice film die. The transport hose and die were controlled to 157° C. and 159° C., respectively. The molten gel blend was extruded into a nip formed by two polished steel rolls gapped at 0.25 mm and controlled to 106° C. A polyester (PET) knitted fabric (Lamports Filter Media, Inc, Cleveland, Ohio) having 0.8 mm by 0.7 mm (0.56 mm$^2$) rectangular open apertures, 0.20 mm thickness and 0.15 m width was fed into the nip at 1.4 m/min speed. As the fabric exited the molten gel blend/nip the article was cooled in air before being wound up with an inserted paper release liner. Upon cooling, a coated fabric having 78 g/m$^2$ coating weight and 0.75 mm by 0.6 mm (0.45 mm$^2$) rectangular open apertures was obtained. Examples 2 and 3 were prepared in the same manner only using Gel lot 2 and SALCARE Lot 2 for example 2 and Gel lot 3 and SALCARE Lot 3 for Example 3. Table 4 contains the process conditions and Table 5 contains the compositional information for Examples 1-3:

TABLE 4

Examples 1-3 process conditions

| Ex. | SIS Input (Barrel Section) | SALCARE Input (Barrel Section) | TSE Temp. (° C.) | Transport Hose/Die Temp. (° C.) | Steel Roll Temp. (° C.) | Steel Roll Gap (mm) | Coating Speed (m/min) | Coating Weight (gr/m$^2$) |
|---|---|---|---|---|---|---|---|---|
| 1 | 1 | 3 | 149 | 157/159 | 106 | 0.25 | 1.4 | 78 |
| 2 | 1 | 3 | 149 | 157/159 | 106 | 0.25 | 1.4 | 78 |
| 3 | 2 | 4 | 121 | 121 | 110 | 0.37 | 2.1 | 83 |

TABLE 5

Examples 1-3 compositions

| Ex. | SIS gel Type (Lot #) | SIS (wt. %) | SALCARE SC95 Wt % (SALCARE Lot #) | KAYDOL oil (wt. %) | AgNO$_3$ (wt. %) | NaOH (wt. %) | DI H2O (wt. %) |
|---|---|---|---|---|---|---|---|
| 1 | Linear (1) | 15.0 | 38.0 (1) | 45.0 | 0.8 | 0.08 | 1.12 |
| 2 | Linear (2) | 18.0 | 37.6 (2) | 42.0 | 0.8 | 0.16 | 1.44 |
| 3* | Radial (3) | 18.0 | 38.2 (3) | 41.4 | 1.6 | 0.24 | — |

*Example 3 also contains IRGANOX 1010 at 0.6 wt %.

Preparation of Example 4

Example 4 was prepared by soaking Example 1 in the aqueous silver (I) oxide solution for two minutes. The soaked film was then placed in an oven operating at 100° C. for 30 minutes.

Testing of Example 3 Adhesion

Example 3 (the gel coated PET fabric) and slabs (1 mm thick) having the composition of Example 3 were tested for 180° peel adhesion from stainless steel using the peel adhesion test. Measurements of the instantaneous peel force was measured for two 0.13 m long samples and averaged. The 180° peel adhesion from stainless steel was 0.0 N/cm for both the slab and gel coated PET fabric of Example 3. The extremely low 180° peel adhesion demonstrate the inability of the composition and articles of the invention to form a strong adhesive bond. These low values, for the composition and article, are considered to be non-adhesive or non-adherent.

Testing of Examples 1-3 Absorbency

Examples 1-3 were tested for their ability to absorb 0.8 wt. % NaCl (saline) as outlined in the Saline Absorbency test. Table 6 contains the amount of saline absorbed as a function of time.

TABLE 6

Saline absorbency vs. time for Examples 1-3

| Ex. | SIS gel Type (Lot #) | SIS (wt. %) | SALCARE Type (Lot #) | 0.5 hour Saline Absorb. | 1 hour Saline Absorb. | 2 hours Saline Absorb. | 6 hours Saline Absorb. | 24 hours Saline Absorb. |
|---|---|---|---|---|---|---|---|---|
| 1 | Linear (1) | 15.0 | SC95 (1) | 0.9 | 1.7 | 1.5 | 1.6 | 1.8 |
| 2 | Linear (2) | 18.0 | SC95 (2) | 2.9 | 2.9 | 3.1 | 2.0 | 2.2 |
| 3 | Radial (3) | 18.0 | SC95 (3) | 2.4 | 2.8 | 2.8 | nm | nm | nm—not measured

The saline absorbency data demonstrates that the composition and article of the invention can absorb an amount of saline that is 1-3 times their dry weight. All samples remained intact after saline exposure.

Optical micrographs of Example 1 before and after 2 hours of saline exposure were obtained at 2.5× magnification in reflection mode and analyzed for the size of the aperature by measurements of the resulting micrographs. The aperature area was 0.45 mm2 as coated and 0.35 mm2 in the equilibrium saline hydrated state for Example 1.

Testing of Examples-Antimicrobial Performance

Example 3 was tested for antimicrobial anti microbial performance against *Staph. Aureus* using the Zone of Inhibition Test. Example 3 was sterilized using a cobalt-γ source at both 25 and 40 kilograys (kGy). The samples were tested in the dry state. All samples had a diameter of 24 mm. Table 7 contains the results from the Zone of Inhibition Test for Example 3 at two sterilization exposure levels and a commercially available silver dressing, Example 5 (Comparative-ACTICOAT available from Smith and Nephew, Largo, Florida).

Example 3 was tested for anti-microbial performance against *Staph. Aureus* using the Zone of Inhibition Test. Example 3 was sterilized using a cobalt-γ source at both 25 and 40 kilograys (kGy). The samples were tested in the dry state. All samples had a diameter of 24 mm. Table 7 contains the results from the Zone of Inhibition Test for Example 3 at two sterilization exposure levels and a commercially available silver dressing, Example 5 (Comparative-ACTICOAT available from Smith and Nephew, Largo, Fla.).

TABLE 7

Zone of inhibition test results for Examples 3 and 5

| Example | SIS (wt. %) | SALCARE Type (wt. %) | KAYDOL oil (wt. %) | $AgNO_3$ (wt. %) | NaOH (wt %) | 20 KGy ZOI (mm) | 40 KGy ZOI (mm) | Ave. ZOI (mm) |
|---|---|---|---|---|---|---|---|---|
| 3 | 18.0 | SC95 (38.2) | 41.4 | 1.6 | 0.24 | 3.4 | 3.8 | 3.6 |
| 5 (Comp) | — | — | — | — | — | — | — | 3.3 |

The silver containing dressings of Example 3 has a higher measured ZOI than the Example 5, the commercially available dressing. The relative amount of total silver in a one square inch portion of dressing is 0.9 milligrams (mg) of $AgNO_3$ (0.6 mg $Ag^+$) in Example 3, calculated from the known material input amounts and coating weight, and 2.9 mg total silver (1.3 mg ammonia soluble silver—the "active" form) for the Example 5(Wounds 10(6), 179-188, 1988 Health Management Publications). Example 3 dressing has significantly less silver, either total or active form and stills performs better in the ZOI test than the comparative example.

Examples 1, 2 and 4 were tested using the % Live Bacteria Test. Samples having a diameter of 0.125 inches (3.2 mm) were placed in contact with 7 mls of bacterial solution having approximately $10^8$ counts of bacteria. Table 8 contains the results of the % Live Bacteria Test at 2 hours of contact of Examples 1, 2 and 4 with the bacterial solution.

TABLE 8

Results from % Live Bacteria Test for Dressings

| Ex. # | Example Description | % Live 2 hrs |
|---|---|---|
| 1 | SIS gel- $AgNO_3$/NaOH Molar Ratio 1/0.5 | 17.5 |
| 2 | SIS gel- $AgNO_3$/NaOH Molar Ratio 1/0.9 | 12.9 |
| 4 | Ex. 1 treated with $Ag_2O$ solution | 1.1 |
|   | Bacteria only | 97.0 |

Preparation of Examples 6-10

Comparative Example 6 was prepared by mixing 100 grams of a cationic dispersion (SALCARE SC95) with 4 milliliters (mL) of 5.6 M $AgNO_3$ at approximately 1000 rpm using a 5.08 cm diameter, three-blade stainless steel paddle that was powered by an air-drive. The 5.6 M $AgNO_3$ was added drop-wise over 10 minutes. The emulsion was mixed for an additional 10 minutes and subsequently vacuum dried at 60° C. and a pressure of 50.8 of mercury for 5 hours. Example 7 was prepared in the same manner as Comparative Example 6 except that 3 mL of 5.6 M NaOH were added drop-wise over 10 minutes after the 5.6 M $AgNO_3$ was added. Example 8 was prepared in the same manner as Example 7 except that an anionic dispersion (SALCARE SC91) was used in place of the cationic dispersion (SALCARE SC95) and the solution was exposed to an air convection oven at 130° C. for 30 minutes instead of evacuating the DI water under temperature and vacuum. Example 9 was prepared in the same manner as Example 8 except that 4 mL of 5.6M $AgNO_3$ and 4 mL of 5.6M NaOH were added to the dispersion. Example 10 was prepared in the same manner as Example 8 except that 3.9 mL of 10 wt. % $H_2O_2$ was added to the blend before air convection oven exposure. Table 9 contains the compositional information for Comparative Example 6 and Examples 7-10.

TABLE 9

Composition of Examples 6-10

| Ex. | SALCARE SC95 (wt. %) | SALCARE SC91 (wt. %) | AgNO$_3$ (wt. %) | NaOH (wt. %) | H$_2$O$_2$ (wt. %) | DI H2O (wt. %) | Final Treatment |
|---|---|---|---|---|---|---|---|
| 6(Comparative) | 96.3 | — | 3.7 | — | — | — | 60° C., 0.7 atm (5 hrs) |
| 7 | 95.5 | — | 3.6 | 0.9 | — | — | 60° C., 0.7 atm (5 hrs) |
| 8 | — | 94.0 | 1.8 | 0.4 | — | 3.8 | 130° C. (0.5 hrs) |
| 9 | — | 88.7 | 3.4 | 0.8 | — | 7.1 | 130° C. (0.5 hrs) |
| 10 | — | 90.4 | 1.7 | 0.4 | 0.4 | 7.1 | 130° C. (0.5 hrs) |

Comparative Example 6 and Examples 7-10 were tested for antimicrobial activity against *Staph. aureas* using the % Live Bacteria Test. One drop of the Example dispersions was dripped into the bacterial solution and mixed. The % live bacteria at 2 hours was measured. All bacterial solution volumes were 7 mL. The initial live bacteria concentration was $1.0 \times 10^8$ bacteria/mL. The results are tabulated in Table 10.

TABLE 10

Results from % Live Bacteria Test

| Example | Sample Weight (g) | % Live after 2 hours |
|---|---|---|
| 6(Comparative) | 0.017 | 27.9 |
| 7 | 0.030 | 1.7 |
| 8 | 0.014 | 5.8 |
| 9 | 0.019 | 0.7 |
| 10 | 0.016 | 4.5 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polymer composition comprising:
   a continuous hydrophobic phase comprising a mixture comprising:
      a hydrophobic liquid comprising mineral oil; and
      a hydrophobic thermoplastic elastomeric polymer;
   absorbent hydrophilic microparticles dispersed within the hydrophobic liquid, wherein the hydrophilic microparticles comprise a crosslinked carboxylic acid-containing organic polymer; and
   a bioactive agent having a particle size less than one micron dispersed in the hydrophilic microparticles, wherein the bioactive agent is selected from the group consisting of a metal oxide of silver, a metal oxide of copper, a metal oxide of zinc, and combinations thereof;
   wherein the polymer composition is nonadherent and contains less than 1 wt % water based on the total weight of the composition.

2. The polymer composition of claim 1 wherein the absorbent hydrophilic microparticles have an average particle size of 10 microns or less, when in a nonhydrated form.

3. The polymer composition of claim 2 wherein the absorbent hydrophilic microparticles have an average particle size of 1 micron or less, when in a nonhydrated form.

4. The polymer composition of claim 3 wherein the absorbent hydrophilic microparticles have an average particle size of 0.5 micron to 1 micron when in a nonhydrated form.

5. The polymer composition of claim 2 further comprising secondary absorbent particles having an average particle size of greater than 10 microns when in a nonhydrated form.

6. The polymer composition of claim 5 wherein the secondary absorbent particles having an average particle size of greater than 10 microns are superabsorbent.

7. The polymer composition of claim 1 wherein the microparticles are superabsorbent.

8. The polymer composition of claim 1 wherein the carboxylic acid-containing organic polymer comprises a copolymer of sodium acrylate and acrylic acid.

9. The polymer composition of claim 1 wherein the thermoplastic elastomeric polymer is selected from the group consisting of a styrene-isoprene block copolymer, a styrene-(ethylene/butylene) block copolymer, a styrene-(ethylene/propylene) block copolymer, a styrene-isoprene-styrene block copolymer, a styrene-butadiene block copolymer, a polyetherester, a poly-alpha-olefin based thermoplastic elastomeric polymer, an ethylene-1-octene copolymer, and combinations thereof.

10. The polymer composition of claim 9 wherein the thermoplastic elastomeric polymer is selected from the group consisting of styrene-isoprene-styrene (SIS), styrene-butadiene-styrene (SBS), styrene-ethylene-propylene-styrene (SEPS), styrene-ethylene-butylene-styrene (SEBS), and combinations thereof.

11. The polymer composition of claim 1 further comprising an additive selected from the group consisting of a plasticizer, a crosslinking agent, a stabilizer, an extruding aid, a filler, a pigment, a dye, a swelling agent, a foaming agent, a chain transfer agent, and combinations thereof.

12. The polymer composition of claim 1 wherein the microparticles are present in an amount of 1 wt-% to 60 wt-%, based on the total weight of the polymer composition.

13. The polymer composition of claim 1 wherein the composition is stable.

14. The polymer composition of claim 1 wherein the composition is in the form of a hydrocolloid.

15. The polymer composition of claim 1 further comprising a swelling agent.

16. The polymer composition of claim 1 wherein the bioactive agent is silver oxide.

17. A medical article comprising the polymer composition of claim 1.

18. A polymer composition comprising:
- a continuous hydrophobic phase comprising a mixture comprising:
  - mineral oil; and
  - a hydrophobic thermoplastic elastomeric polymer selected from the group consisting of styrene-isoprene-styrene (SIS), styrene-butadiene-styrene (SBS), styrene-ethylene-propylene-styrene (SEPS), styrene-ethylene-butylene-styrene (SEBS), and combinations thereof;
- absorbent hydrophilic microparticles dispersed within the mineral oil, wherein the hydrophilic microparticles comprise a crosslinked carboxylic acid-containing organic polymer; and
- a bioactive agent having a particle size less than one micron dispersed in the hydrophilic microparticles, wherein the bioactive agent is selected from the group consisting of a metal oxide of silver, a metal oxide of copper, a metal oxide of zinc, and combinations thereof;
- wherein the polymer composition is nonadherent and contains less than 1 wt % water based on the total weight of the composition.

19. The polymer composition of claim 18 wherein the bioactive agent is silver oxide.

20. The polymer composition of claim 18 wherein the carboxylic acid-containing organic polymer comprises a copolymer of sodium acrylate and acrylic acid.

21. A medical article comprising the polymer composition of claim 18.

22. A polymer composition comprising:
- a continuous hydrophobic phase comprising a mixture comprising:
  - mineral oil; and
  - a hydrophobic thermoplastic elastomeric polymer selected from the group consisting of styrene-isoprene-styrene (SIS), styrene-butadiene-styrene (SBS), styrene-ethylene-propylene-styrene (SEPS), styrene-ethylene-butylene-styrene (SEBS), and combinations thereof;
- absorbent hydrophilic microparticles dispersed within the mineral oil, wherein the hydrophilic microparticles comprise a crosslinked a copolymer of sodium acrylate and acrylic acid; and
- silver oxide having a particle size less than one micron dispersed in the hydrophilic microparticles;
- wherein the polymer composition is nonadherent and contains less than 1 wt % water based on the total weight of the composition.

23. A medical article comprising the polymer composition of claim 22.

* * * * *

UNITED STATES PATENT AND TRADEMARK OFFICE
CERTIFICATE OF CORRECTION

| | |
|---|---|
| PATENT NO. | : 7,745,509 B2 |
| APPLICATION NO. | : 10/728439 |
| DATED | : June 29, 2010 |
| INVENTOR(S) | : Scott A Burton |

It is certified that error appears in the above-identified patent and that said Letters Patent is hereby corrected as shown below:

Column 4
Line 43; Delete "polysaccaridcs" and insert -- polysaccharides --, therefor.
Line 46-47; Delete "Furcelleran" and insert -- Furcellaran --, therefor.
Line 61; Delete "2-acrylamideo-2-" and insert -- 2-acrylamide-2- --, therefor.

Column 12
Line 1-2; Delete "tertraborate," and insert -- tetraborate, --, therefor.
Line 5; Delete "tartarate," and insert -- tartrate, --, therefor.

Column 14
Line 42-43; Delete "tertraborate," and insert -- tetraborate, --, therefor.

Column 16
Line 64-65; Delete "(methychloride" and insert -- (methylchloride --, therefor.

Column 17
Line 6; After "solution" insert -- . --.
Line 15; After "solution" insert -- . --
Line 23; Delete "Mallinkrodt" and insert -- Mallinckrodt --, therefor.
Line 62; Delete "Franidin" and insert -- Franklin --, therefor.

Column 18
Line 24; Delete "(15x100 rein)." and insert -- (15x100 mm). --, therefor.

Column 21
Line 3; (Table 4), Delete "SIS Input" and insert -- SIS Gel Input --, therefor.

Signed and Sealed this
Twenty-second Day of March, 2011

David J. Kappos
*Director of the United States Patent and Trademark Office*

CERTIFICATE OF CORRECTION (continued)
U.S. Pat. No. 7,745,509 B2

Column 22
Line 66; Delete "aperature" and insert -- aperture --, therefor.
Line 67; Delete "aperature" and insert -- aperture --, therefor.

Column 23
Line 8; After "antimicrobial" delete "anti microbial".

Column 25
Line 20; Delete "aureas" and insert -- Aureus --, therefor.